United States Patent [19]

Saxena

[11] Patent Number: 4,833,083
[45] Date of Patent: * May 23, 1989

[54] PACKED BED BIOREACTOR

[75] Inventor: Vinit Saxena, Pinole, Calif.

[73] Assignee: Sepragen Corporation, San Leandro, Calif.

[*] Notice: The portion of the term of this patent subsequent to Dec. 9, 1993 has been disclaimed.

[21] Appl. No.: 54,262

[22] Filed: May 26, 1987

[51] Int. Cl.[4] .......................... C12N 5/00; C12M 1/40; C12M 3/00
[52] U.S. Cl. .................. 435/240.24; 435/240.23; 435/288; 435/284; 210/617; 210/618
[58] Field of Search ............... 435/240.23, 240.24, 435/288, 284, 285, 311, 299; 210/617, 618, 150, 151

[56] References Cited

U.S. PATENT DOCUMENTS

| 2,082,322 | 6/1937 | Brundage | 210/266 X |
|---|---|---|---|
| 2,110,318 | 3/1938 | Baruch | 210/287 |
| 3,204,770 | 9/1965 | Brink | 210/287 X |
| 3,212,641 | 10/1965 | Komarmy et al. | 210/266 |
| 4,144,136 | 3/1979 | Corbeil | 435/285 |
| 4,220,725 | 9/1980 | Knazek . | |
| 4,225,671 | 9/1980 | Punchinger et al. | 435/285 X |
| 4,279,753 | 7/1981 | Nielson et al. . | |
| 4,391,912 | 7/1983 | Yoshida et al. . | |
| 4,442,206 | 4/1984 | Michaels et al. . | |
| 4,496,461 | 1/1985 | Leeke et al. . | |
| 4,546,083 | 10/1985 | Meyers et al. | 435/285 X |
| 4,603,109 | 7/1986 | Lillo . | |
| 4,627,918 | 12/1986 | Saxena | 210/656 |
| 4,683,062 | 7/1987 | Krovak et al. | 210/150 X |

FOREIGN PATENT DOCUMENTS

| 1009278 | 1/1986 | Japan | 435/311 |
|---|---|---|---|
| 111195 | 11/1917 | United Kingdom | 210/117 |

Primary Examiner—Robert E. Garrett
Assistant Examiner—Carl D. Price
Attorney, Agent, or Firm—Shyamala T. Rajender

[57] ABSTRACT

A bioreactor for anchorage or nonanchorage dependent cells or for immobilized enzymes that is capable of achieving high cell densities or concentrations of reaction products is disclosed. The bioreactor is capable of being easily scaled up. The bioreactor utilizes horizontal or radial flow of the culture or growth medium across a packed bed of microcarriers with attached cells or enzymes. The radial flow utilized by the chamber minimizes the non-optimal culture perfusion problems and maximizes the uniformity of medium delivery and cell and/or enzyme viability. The cell culture chamber possess the capability for the production of many industrially important and useful products, particularly in the medical, pharmaceutical, food, agricultural, environmental and purification industries. In the medical and pharmaceutical industries, the large scale production of therapeutically important substances such as anti-tumor factors, hormones, viral antigens, enzymes, interferons and other valuable biomolecules, is greatly facilitated.

37 Claims, 7 Drawing Sheets

PACKED BED BIOREACTOR

BACKGROUND OF THE INVENTION

The present invention relates to a packed bed bioreactor and more particularly to a bioreactor which utilizes radial flow of the reaction medium across the packed bed.

In recent years, the use of solid support matrices for homogeneous and heterogeneous catalysis has become quite wide spread, as it facilitates control of the reaction conditions and parameters. In the face of a great deal of demand for certain types of industrially and pharmaceutically significant chemicals, the utilization of individual enzymes and/or multienzyme systems has also expanded to a wide variety of fields. The recent developments in biochemistry and biotechnology, the clarification of the mechanisms of enzyme reactions, development of new sources for various enzymes, combined with the progress in applied microbiology and genetic engineering have markedly accelerated the utilization of enzymes for various industrial processes. As a result of these technological advances and the need for the large scale production of enzymes and enzyme systems, great efforts are being directed to alternative methods for the large scale production of enzymes, rather than the traditional, tedious, time-consuming and laborious processes of producing and extracting these enzymes from naturally occurring animal and/or microbial sources, and combating problems associated with the inactivation and/or "poisoning" of these enzymes by other components of the cell systems from which they have been extracted. Methods have been developed for the direct immobilization of whole microbial or mammalian cells on inert supports and directing reaction media through such immobilized cells, whereby the enzymes contained in the cells react with the media and produce the desired products, without contamination by other cell components. Such immobilization techniques are discussed in "Immobilized Cells In Preparation Of Fine Chemicals", I. Chibata et al., "Advances in Biotechnological Processes", I, pp 203–222, 1983, published by Alan R. Liss, Inc., 150 Fifth Avenue, New York, N.Y.

Current interest in the use of biologically derived substances as therapeutic and diagnostic agents in medicine has stimulated research into improved methods for the production of these substances. Since naturally occurring biomolecules are usually present at low levels in animal and microbial sources, and because it is logistically difficult to increase production by adding more and more animals or microbial cells to a manufacturing protocol, process scale-up in vivo is very difficult and impractical. In the case of bioengineered products, there is a need for efficient expression systems for the production of recombinant-DNA proteins. These considerations have led to the development of bacterial and mammalian cell culture systems for the large-scale production of industrially useful and therapeutically valuable biomolecules.

As a result, substantial efforts have been directed to the large scale, relatively fast growth of whole naturally occurring and/or genetically altered cells, for various industrial uses. These efforts have resulted in the development of various types of bioreactors for the growth of cells and/or for the immobilization of isolated enzymes and enzyme systems. The following U.S. patents exemplify some of the different types of bioreactors used for various applications and the problems associated with each of these reactors:

U.S. Pat. Nos. 4,220,725 issued Sept. 2, 1980 to R.A. Knazek et al; 4,279,753 issued July 21, 1981 to N.E. Nielson et al; 4,391,912 issued July 5, 1983 to K. Yoshida et al; 4,442,206 issued Apr. 10, 1984 to A.S. Michaels et al; and 4,603,109 issued July 19, 1986 to E. Lillo. The U.S. Pat. No. 4,603,109 issued to Lillo sets forth the a discussion of the various bioreactor systems including the vat-type, the packed column-type, the porous membrane-type and a porous ceramic matrix-type reactors, wherein the reaction solution in introduced into an annular bore through a ceramic matrix member and the product solution is collected from the outside of the ceramic matrix member.

Various reaction schemes in which bioreactors have been utilized may be broadly classified into six major categories schematically represented as follows:

| | | | |
|---|---|---|---|
| 1. Catalytic Reactor | Reactants | column packed with catalyst | Product |
| 2. Enzyme Bioreactor - I | Substrate | enzyme immobilized on matrix | |
| 3. Enzyme Bioreactor - II | Substrate | cells containing enzyme immobilized on matrix | Product |
| 4. Cell Culture Bioreactor | Nutrients + 02 | non-adherent cells immobilized by cross-linking on matrix | Product + Waste |
| 5. Cell Culture Bioreactor - II | Nutrients + 02 | adherent cells growing on matrix | Product + Waste |
| 6. Extra Corporeal Shunt | Plasma or other fluid from patient | absorption or affinity bed | purified plasma or fluid returned to patient |

For cell culture, represented in reactions 4 and 5 above, there are two basic cell types that are used in mammalian cell bioreactors—suspension cells and anchorage-dependent cells. Suspension cell lines can often be grown using modifications of classical technology, such as the stirred-tank reactor, originally developed for the growth of bacterial and yeast cells in the fermentation industry. For certain applications, these suspension cells may also be conveniently cross-linked to a solid matrix or trapped inside a suitable "holding" molecule, rather than grow them in a suspension mode.

The culture technology for anchorage-dependent or adherent cells is more sophisticated. Anchorage-dependent cells produce many substances of commercial interest but are much more difficult to grow than suspension cells. They require a solid support to which they can attach before any growth or division can occur. Their requirement of cell attachment results in some handling difficulties. They ar also generally more demanding in their nutritional requirements than are suspension cells. As a result, a number of new techniques are being developed for the large-scale production of anchorage-dependent cells, with varying degrees of success., depending on the particular cell line used. Each of these techniques, however, suffers from significant drawbacks. Therefore, there exists a great need for improved devices for the large-scale growth of anchorage-dependent cells which increase their viability and ease of handling.

Conventional large-scale production of anchorage-dependent or adherent cells uses glass of plastic roller bottles, derivatives of the flasks used in laboratory-scale research. But, roller bottles have a relatively low surface area for cell growth, are unwieldy to use in large numbers or sizes and are relatively labor-intensive. In an effort to increase the surface area, methods have been devised whereby glass spheres (diameter of 2-3 mm) are packed in a column and inoculated with the cell culture. Fluid pumps circulate nutrients from an external medium reservoir. Oxygen tension and pH need to be carefully controlled. The nutrient medium flow in this type of a glass bead bioreactor is generally from the bottom of the column, through the beads and cells, to the top of the column, where it is drawn off and recirculated. This type of flow through the length of the entire chamber can be termed longitudinal forced flow. It results in a polarized column where the culture medium encountered by the cells at the top has been partially depleted of nutrients and has a higher concentration of waste products. Furthermore, scaling up this type of column is fraught with difficulties associated with the necessity for cleaning the beads with strong acid before each use, the possibility of the increased weight of the glass beads damaging the cells, and the logistical problems caused by the shear number of beads needed for large sized columns.

A substantial advance in high-yield culture of anchorage-dependent cells has been achieved with the introduction of microcarrier heads, small spheres of dextran, agar, gelatin, polystyrene or polyacrylamide, on whose surfaces, cells can attach and grow. The microcarriers are placed in a tank-type culture vessel with the culture or growth medium and kept in suspension with gentle stirring. However, even this advanced technique presents certain procedural problems. The necessity for suspension and mixing creates handling problems. The cells are subjected to mechanical stress which might result in cell rupture. There is also a problem associated with the transfer of oxygen that is characteristic of stirred-tank reactors. In order to prevent settling of the cells out of suspension, the microcarrier density must be severely limited.

Another alternative prior art method for the large-scale culture of cells is the use of hollow fiber cartridges. Each cartridge is composed of many long, narrow polysulfone, polypropylene or polyester fibers running in parallel. The fibers are embedded at both ends in a cylindrical housing, and the device is enclosed within a plastic shell. The cells are housed on the outside of the fibers and culture medium flows longitudinally through the bores of the hollow fibers. Hydrostatic pressure differences cause some of the medium to penetrate the fiber walls and bathe the cells, which have been deposited outside the fibers in the extracapillary space. Eventually, this secondary nutrient flow returns to the lumena of the fibers and exits the cartridge.

There are, however, a number of drawbacks to this method also. The longitudinal flow of the medium results in a pressure drop from one end to the other end of the cartridge. This pressure drop produces severe gradients in the distribution of nutrients and waste products such that the culture growth is not uniform throughout the cartridge. In addition, limited or restricted circulation in the extracapillary space leads to the formation of microenvironments and anoxic pockets of nonviable cells. Finally, occlusion of the fibers by cell growth can interfere with the mass transfer of nutrients and oxygen to the cell colonies. These problems are enhanced by and during process scale-up; the bigger the cartridges, the greater is the influence of the pressure drop, anoxic pockets and microenvironments. Rather than increase fiber unit size, it appears more feasible to place numerous small cartridges in a parallel configuration.

A relatively new development in culture technology is the use of a honeycombed ceramic matrix for the cultivation of anchorage-dependent cells. The ceramic is manufactured in the form of a cylindrical cartridge and contains numerous square channels that run in parallel throughout the length of the device. Medium flow is longitudinal and in direct contact with the cells that have adhered to the ceramic. The longitudinal flow of this unit can also set up nutrient gradients similar to those noted earlier with the glass bead and hollow fiber reactors. The major problem in using and evaluating the ceramic matrix as a culture chamber is that it is only available as part of an expensive bioreactor system and has not been widely distributed or available for widespread use.

Commercially valuable biomolecules derived from cultured cells, or enzymes are usually secreted in minute quantities. Therefore, the highest possible cell densities or concentrations and largest-scale cultures are needed to achieve economical and large quantity production of these substances of interest. Since the role of cultured cells and enzymes in the production of valuable molecules is likely to increase in the near future, efficient means for their production, propagation and utilization is of paramount importance. In the case of anchorage-dependent cells, new culture methods and devices which would help in the elimination of the problems of low growth-surface area, low cell yield, unequal distribution of nutrients, and inefficient scale-up is essential. In the case of enzymes, methods and devices which maximize their catalytic efficiency and viability are highly desirable. Thus a need exists for a device and method which can be easily adapted for use as a chemical reactor, a bioreactor, a cell culture chamber or reactor, or as an extra corporeal shunt and which also successfully addresses, minimizes and/or eliminates the problems of the prior art devices.

Therefore, it is an object of this invention to provide an improved bioreactor which is easily adaptable for reactions involving cells or cell components or inorganic or organic catalysts including enzymes or enzyme systems.

A further object of the invention is to provide a cell culture growth chamber for anchorage-dependent cells.

Another object of the invention is to provide a cell culture growth chamber for animal, plant or microbial cells.

Still another object of the invention is to provide a cell culture growth chamber for cells in suspension or nonanchorage-dependent cells.

Yet another object of the invention is to provide a bioreactor which utilizes a radial or horizontal flow of culture or reaction medium across a packed bed of support material.

Still another object of the invention is to provide a cell growth chamber which eliminates the problems of a low growth surface area, low cell yield and unequal distribution of nutrients to the cell culture.

Another object of the invention is to provide a cell culture growth chamber that is capable of achieving high cell densities and which can be easily scaled up, while providing uniform distribution of the culture medium.

Another object is to provide an enzyme bioreactor which maximizes the enzyme efficiency and the life time of the enzyme.

Yet a further object of the invention is to provide a growth chamber for large-scale preparation of anchorage-dependent cell culture.

Another object of the invention is to provide a bioreactor having the capabilities of commercial application in the production of medically relevant, enzyme or cell-culture-derived molecules such as anti-tumor factors, hormones, therapeutic enzymes, viral antigens, interferons and other substances.

Yet another object of the invention is to provide a bioreactor which utilizes a radial or horizontal flow of culture or reaction medium across a packed bed of microcarriers or other support matrices with enzymes or enzyme systems attached thereto for reaction with selected substrates of choice.

Another object of the invention is to provide a bioreactor having the capabilities of commercial application in the production of commercially viable, cell-culture-dependent or chemically catalyzed or enzyme-catalyzed reaction products in the food, agriculture, oil and other industries.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects and in accordance with the purpose of the present invention as embodied and broadly described herein, the present invention is directed to a bioreactor which utilizes radial flow of the reaction medium therethrough and which thereby achieves uniform distribution of the medium therethrough. Key features of the bioreactor of this invention are: increased surface area compared to prior art bioreactors, uniform distribution of the reaction medium, horizontal or radial flow of the medium, ease of production scale-up, ability to use soft, inexpensive support matrix materials, increased product recovery, high flow rates, and low pressure drop. The bioreactor of this invention is particularly applicable for large-scale applications in the commercial production of biologically and/or therapeutically important molecules using cells, cell cultures, cell components, enzymes, enzyme systems and the like.

As used herein, the term "bioreactor" refers variously, without limitation, to a packed bed chamber or reactor which employs horizontal or radial flow of the culture or reaction medium therethrough and which may be used for the growth of cell cultures or for packing with suitable support materials or matrices such as, for example, microcarriers and the like, to which cell colonies of cell components may be attached or on which individual, isolated enzymes or enzyme systems may be immobilized for reaction with selected substrates. The term is used interchangeably herein for the general description of the basic device or in the description of specific use, depending on the particular use contemplated.

The bioreactor of this invention comprises a vessel having at least one removable end section and containing a packed bed of a support or matrix material such as, for example, microcarriers and the like, with cells or cell components attached thereto or with individual, chemical catalysts or isolated enzymes or enzyme systems immobilized on the support or matrix material. As used herein, the terms "enzyme" or "enzyme system" include without limitation, a single enzyme, a plurality of enzymes, a multienzyme system, an enzyme and its cofactors and/or prosthetic groups, if any, and enzymes in combination with any other molecules or entities. The culture or reaction medium, in one illustrated embodiment, enters a top center inlet port, (the inlet port can be located on the side also), flows radially out from the center via header channels and passes into an outer annular channel, after which the medium passes uniformly through a wall of an outer porous tube and into a middle channel or chamber containing the bed of support material with cells or cell components attached thereto or with catalysts, enzymes or enzyme systems immobilized thereon. The medium flows radially or horizontally inward across the support matrix bed, through a wall of an inner porous tube, and into an inner channel. Spent medium and cell or enzyme products flow down the inner channel and through a collector to the vessel outlet. The outer and inner porous tubes may be made of a filter screen or porous filter material. An inner core may be positioned within the inner porous tube to provide an inner flow channel therebetween.

The invention also provides a cell culture growth chamber for anchorage-dependent or immobilized cells that is capable of achieving high cell densities and which can be easily scaled up. The chamber can be used for the economical production of a number of important therapeutic, diagnostic and other industrially valuable substances and molecules which cannot be produced in large enough quantities from animal tissues or microbial systems.

Commercial application of the bioreactor of this invention may be in the production of medically relevant, cell-culture derived or enzymatically produced molecules, such as for instance, anti-tumor factors, hormones, therapeutic enzymes, viral antigens, and interferons. The present invention provides a bioreactor which is also economical to operate, easy to scale up and considerably more efficient when packed with chemical or biological catalysts to produce other substances which may be valuable in other industrial applications such as the food, agricultural, environmental, petroleum and the purification industries.

In another embodiment, designed for large scale production, a plurality of spaced inner porous tubes and inner channels through which the spend medium, reactants and/or products flow to a collector, are provided.

BRIEF DESCRIPTION OF THE DRAWINGS

The accompanying drawings, which are incorporated and form a part of the specification, illustrate a few embodiments of the invention and, together with the description, serve to explain the principles of the invention.

DETAILED DESCRIPTION OF THE INVENTION

Figure 1:
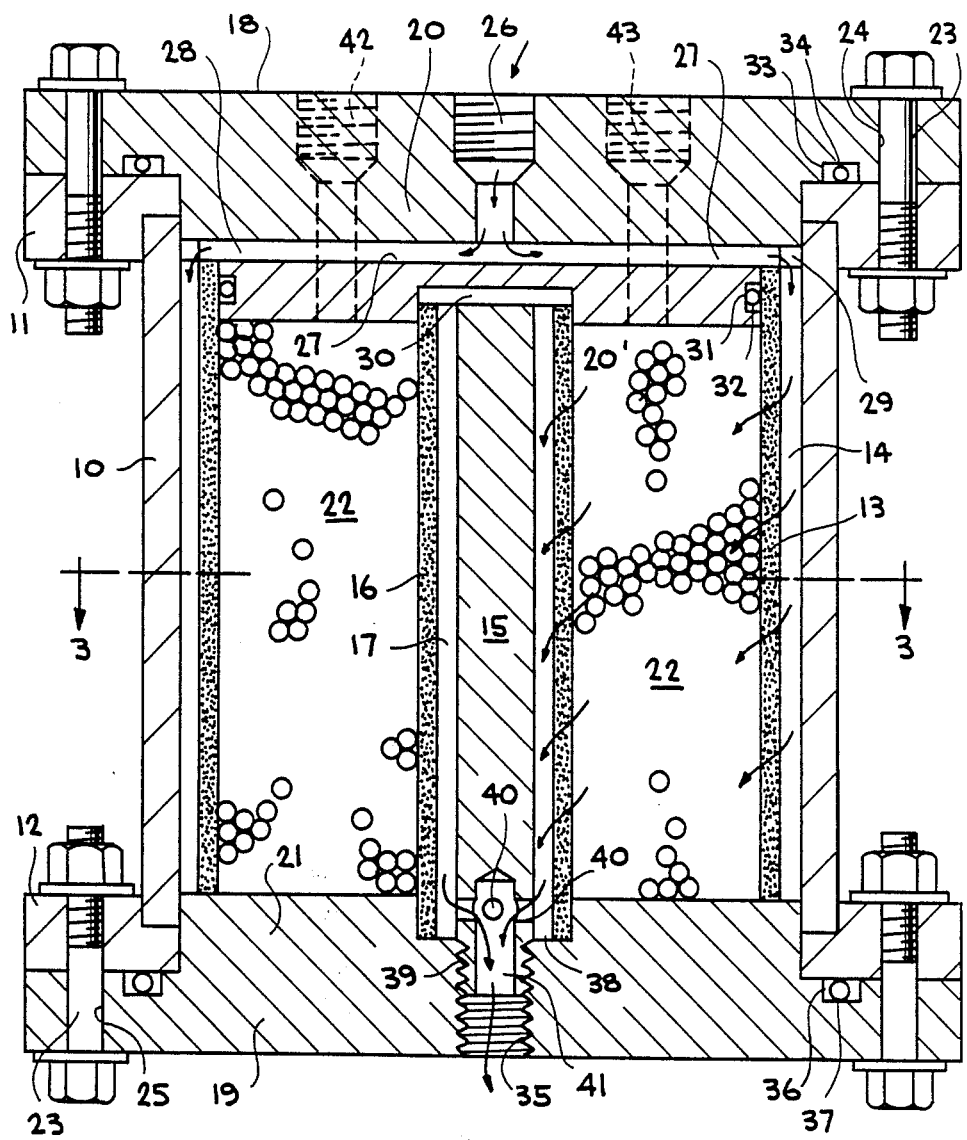
FIG. 1 illustrates in cross-section, an embodiment of a radial flow culture chamber or bioreactor in accordance with the present invention.

The present invention is directed to a bioreactor which is easily adaptable for use as a reactor for a variety of chemical and biological reactions of commercial importance. These include, without limitation, the propagation of anchorage-dependent cell cultures, use of chemical catalysts supported or immobilized on an inert matrix, or enzyme-catalyzed reactions where the enzyme or enzyme system is immobilized on an appropriate support medium. Key features of the bioreactor of the present invention include: (1) increased surface area for cell growth or enzyme adsorption as the case may be; (2) uniform distribution of reaction medium; (3) radial or horizontal flow of the medium; (4) ease of production scale-up; (5) low pressure drop; (6) high flow rates; and (7) increased product recovery. Commercial application of the bioreactor of the invention are in the production of industrially valuable and medically relevant, cell-culture-derived or catalytically produced molecules.

As used herein, the term "bioreactor" refers variously, without limitation, to a packed bed chamber or reactor which employs horizontal or radial flow of the culture or reaction medium therethrough and which may be used for the growth of cell cultures or for packing with suitable support materials or matrices such as, for example, microcarriers and the like, to which cell colonies or cell components may be attached or on which individual, isolated enzymes or enzyme systems may be immobilized for reaction with selected substrates. The term is used interchangeably herein for the general description of the basic device or in the description of specific use, depending on the particular use contemplated. As used herein, the terms "enzyme" or "enzyme system" includes without limitation, a single enzyme, a plurality of enzymes, a multienzyme systems, cells or cell components containing such enzymes or enzyme systems, an enzyme and its cofactors or prosthetic groups, if any, and enzymes in combination with any other molecules or entities.

The bioreactor is of a construction generally similar to the radial flow chromatography column described and claimed in applicant's U.S. Pat. No. 4,627,918 issued Dec. 9, 1986. With certain modifications of the chromatography column and replacement of the bed of fluid separation medium with a packed bed of microcarriers with cells or cell components attached thereto or with enzymes or enzyme systems immobilized thereon, the modified apparatus produces results which overcome the earlier-discussed problems of low cell yield, unequal distribution of nutrients, and inefficient scale up. Furthermore, due to the horizontal or radial flow of the modified apparatus, the problems associated with compaction and damage to the support matrix, especially in the use of microcarrier, caused by the axial flow type apparatus, are overcome. It has been found that the modified radial flow apparatus can be utilized for large-scale, economical production of a number of important therapeutic, diagnostic and other industrially valuable substances which cannot be produced from animal or microbial systems by conventional techniques. The significant advantages resulting from the modified apparatus are primarily attributable to a uniform flow of the culture or reaction medium through the bed of microcarriers in a radial or horizontal direction.

Thus, the vessel or housing of the above-referenced chromatography column can, with some modifications, be used also as an immobilized catalyst or enzyme bioreactor. In this application, an enzyme or enzyme system is immobilized on a solid support, such as diatomaceous earth, silica, alumina, ceramic beads, charcoal, polymeric beads or sheets or glass beads, which are packed in the column to form a bed. The reaction medium is then passed through this packed bed and the catalyst such as an organic or inorganic molecule or an enzyme or enzyme system converts the reactant or substrate contained in the reaction medium into the desired product or products. Traditionally, vertical flow bioreactors suffer from high pressure drops, low flow rates and also gradients in product and reactant concentration set up along the length of the column. The radial flow bioreactor of this invention relieves these problems.

In certain other applications, cells or cell components such as for instance, plasmids, vectors, DNA sequences and the like may also be immobilized on a solid support matrix by cross-linking or by entrapment (as in the case of the production of L-amino acids, glucose, organic acids etc). Such immobilized cells can be grown or cultured advantageously in the radial flow bioreactor of the present invention.

Figure 3:
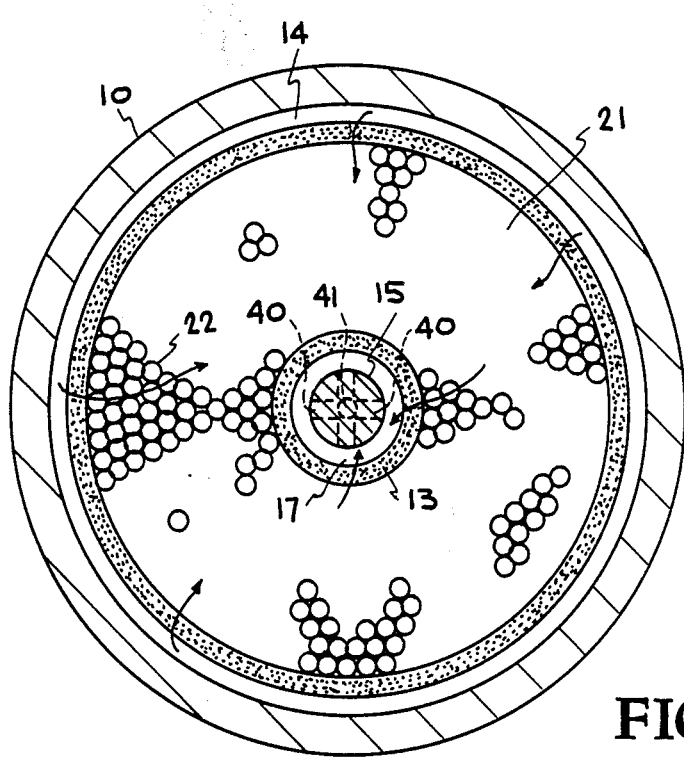
FIG. 3 is a view of the apparatus of FIG. 1 taken along line 2—2 of FIG. 1.
Figure 4:
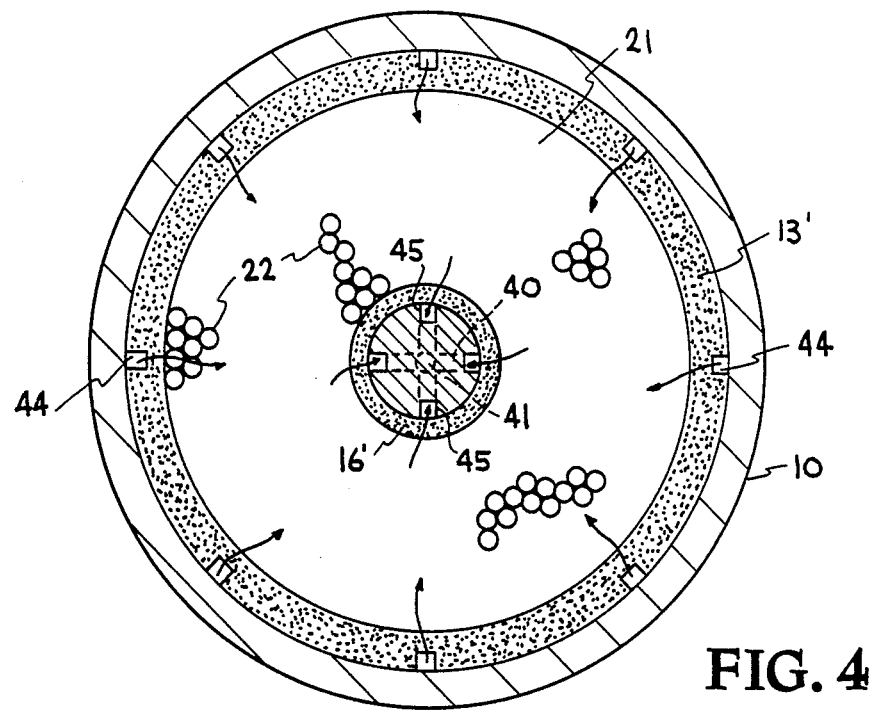
FIG. 4 illustrates a modification of the outer porous member and central core member of the apparatus illustrated in FIG. 3, so as to provide grooved inlet and outlet channels.

As can be seen in the embodiment of the invention as illustrated in FIG. 1, culture or reaction medium enters the vessel or bioreactor via a top center inlet port, flows radially out from the center via header channels and enters an outer annular channel (FIG. 3) or a plurality of equally spaced vertical grooves (FIG. 4). From there, the medium passes through the wall of an outer porous tube or screen-like member and into the middle channel or chamber which contains packed microcarriers and adhered cells or adsorbed enzymes. As used herein, the term "cells" includes, without limitation, intact cells, mammalian or plant or microbial, cultures or innocula of such cells and any and all components of such cells which may be so employed and the term "enzyme" includes, without limitation, single or multiple, isolated enzymes, cells, cell culture or cell components containing the enzymes, enzyme systems which include multiple enzymes, cofactors and/or prosthetic groups. The term "culture medium" includes any medium for the optimal growth of various cell lines employed or any medium for enzyme reactions including but not limited to enzyme substrates, cofactors, buffers, and like necessary for the optimal reaction of the enzyme or enzyme system of choice.

The medium flow radially (horizontally) inward across the packed bed and through the wall of an inner porous tube or screen-like member and into an inner annular channel (FIG. 3) or a plurality of equally spaced grooves (FIG. 4). The spend medium and cell or enzyme products flow down the inner channel and through a collector to the outlet of the vessel or bioreactor.

This radial flow path offers a number of advantages over existing bioreactor methodologies. Since the direction of medium flow is across a transverse or horizontal section of the culture chamber and not through its entire length, the effective bed height of the packed column of cells or microcarriers is the relatively small distance between the outer and inner porous tubes. By restricting the bed height, the length of the flow path of the culture or reaction medium will be kept to a minimum compared to the lengthwise flow of the vertical flow type culture chambers. The radial flow principle results in high flow rates, minimal pressure drops, equal distribution of medium and/or nutrients, and rapid removal of waste products and desired biomolecules or other industrially important molecules.

In addition to flow considerations, there is also the question of maximum cell density. In the radial flow chamber, packing of the middle channel with microcarriers in a static mode provides a very high surface area for cell growth within a very small physical volume of the reactor. The result is that this chamber is able to accommodate cell densities several times greater than other systems and yet maintain good cell viability due to the efficiency of the flow of culture medium.

Figure 5:
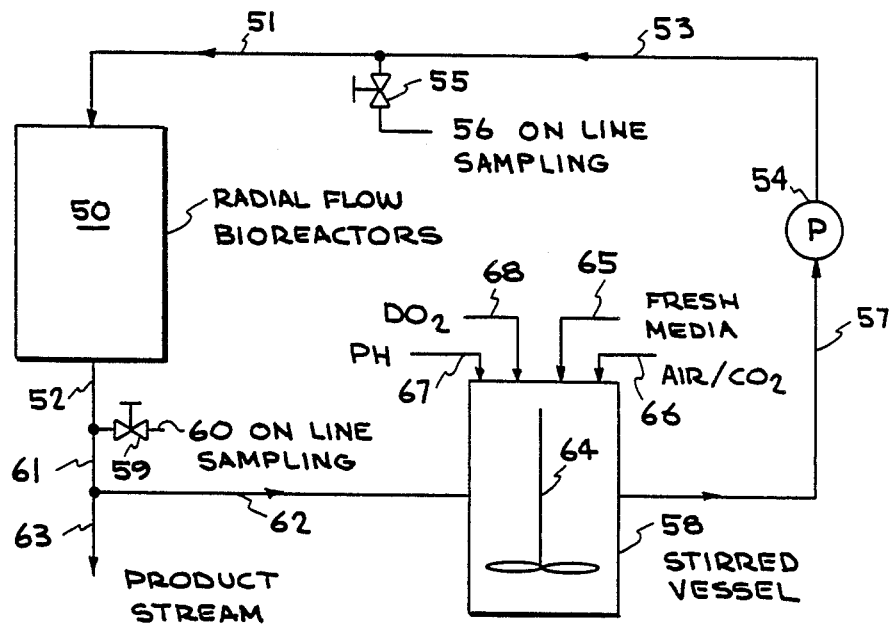
FIG. 5 schematically illustrates a continuous cell-culture system using a radial-flow microcarrier-based bioreactor or culture chamber of FIG. 1.

The culture or reaction medium is pumped from a reservoir, through the cells in a radial flow culture chamber, and back into the reservoir. As shown in FIG. 5, the recirculated medium is monitored for pH, dissolved oxygen content, glucose utilization and lactic acid production or for the desired enzyme products as the case may be.

For cell growth, oxygen and/or carbon dioxide (depending on the cell line used) are bubbled through the medium as needed to maintain proper pH and oxygen content. When the lactic acid content of the medium reaches a critical value (to be determined on the basis of the cell line of choice), the culture medium is replaced with a fresh batch and the growth continued. The culture chamber for most cell growth or enzyme reactions is maintained at about 37° C., but may be changed to suit individual needs and conditions.

Referring now to the drawings, FIG. 1 illustrates an embodiment of a bioreactor or cell culture growth chamber in accordance with the invention. The apparatus of FIG. 1 may utilize a porous tube arrangement, such as those illustrated in FIGS. 3 or 4. In FIG. 3, a pair of spaced porous tubes or screen-like members are positioned to form an outer annular flow channel and an inner annular flow channel. In FIG. 4, the outer porous tube is provided with a plurality of equally spaced vertical grooves through which the culture medium flows prior to passing through the walls thereof into the middle channel. The inner porous tube shown in FIG. 3 is in spaced relation to a central core member to form an inner channel, while in FIG. 4, the inner porous tube fits snugly around the central core member which is provided with a plurality of equally spaced grooves which function as the inner channel to which the spent medium flows after passing through the walls of the inner porous tube. Each of the arrangements illustrated in FIGS. 3 and 4 utilize a horizontal or radial flow of the culture medium as it passes across the packing of support or matrix material in the middle channel of the vessel or bioreactor.

Figure 2:
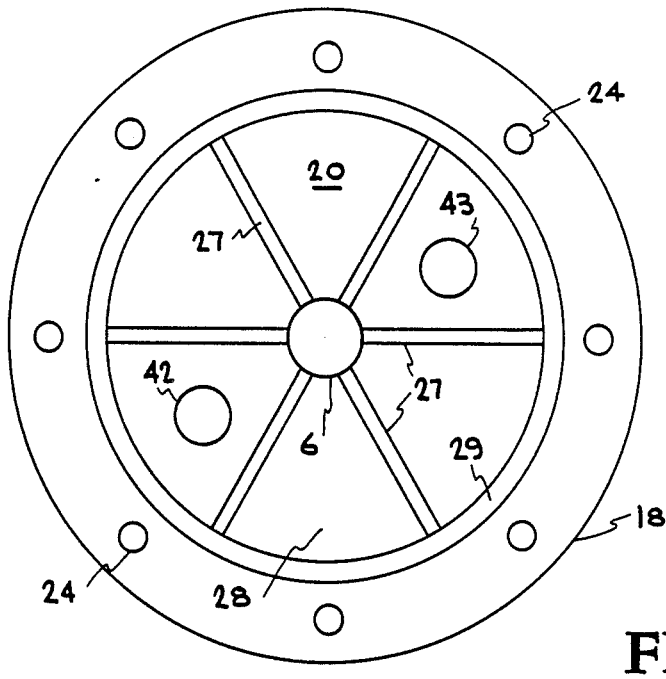
FIG. 2 is a view of the upper end cap of the apparatus of FIG. 1, illustrating the inlet flow distribution system.

The bioreactor of the embodiment illustrated in FIGS. 1–3 basically comprises a cylindrical outer wall, housing or vessel 10 having outwardly extending flanges 11 and 12 secured at opposite ends, a porous tubular member or filter screen 13 located within said outer wall and spaced therefrom to define an outer annular channel or passage 14 therebetween, a cylindrical core or member 15 and a porous tubular member or filter screen 16 located centrally within outer wall 10 and spaced from one another to define an inner annular channel or passage 17 therebetween, an inlet end plate, cap or member generally indicated at 18, an outlet end plate cap or member generally indicated at 19, each including an inwardly protruding sections 20 and 21 and a bed, package or matrix 22 of selected support materials with attached cells or enzymes retained in a middle channel or chamber between tubular members 13 and 16 and protruding section 21 and an inner member or plug 20' located adjacent protruding section 20, with end caps or members 18 and 19 being secured to flanges 11 and 12 respectively, by bolts or other securing means 23, eight (8) used in this embodiment, which extend through openings 24 and 25 in end caps 18 and 19 and aligned openings in flanges 11 and 12 respectively. The porous tubular members 13 and 16 are coaxial with respect to each other and have a permeability compatible with the support or matrix material 22 for allowing a desired flow rate of reaction or culture medium to pass therethrough.

Inlet end cap or plate 18 is provided with a centrally located threaded opening 26 into which a threaded coupling (not shown) is secured and to which is connected a supply (see FIG. 5) of reaction or culture medium. Protruding section 20 of end cap 18 is provided with a plurality of radially extending fluid distribution grooves or channels 27 (see FIG. 2) each terminating at one end of threaded opening 26 and extending radially outwardly along an inner surface 28 of protruding section 20 to an annular groove or cut-away 29 at the periphery of protruding section 20 so as to be in open fluid communication with the outer annular channel or passage 14.

Reaction or culture medium from an external supply passes into opening 26 and is evenly distributed into annular channel 14 via the plurality of radial grooves 27 and annular groove 29. The central opening 26, radial grooves 27, annular groove 29 and annular channel 14 constitute a reaction or culture medium distribution means. In the embodiment illustrated in FIGS. 1–3, the distribution of the reaction or culture medium is carried out by six (6) grooves 27 spaced about 60° apart around the threaded opening 26 and annular channel 14. The number of distribution grooves or channels may be increased or decreased depending upon the purpose for the channels or grooves to provide an even and uniform distribution of the culture or reaction medium around the porous tubular member 13 and through the bed 22. While grooves or channel 27 and 29 are illustrated as being on surface 28 of protruding section 20 of end cap 18, the respective grooves may extend along and around the adjacent or matching surface of inner plug or member 20' or both. In addition, the distribution grooves or channels may be replaced with an annular gap located between protruding section 20 of end cap or plate 18 and inner plug or member 20', or formed in the inner end or surface 28 of protruding section 20 of end cap 18.

Inner plug or member 20' adjacent inlet end cap 18 includes a central countersunk section 30 and an outer annular groove 31, countersunk section 30 extending over an upper end of core 15 and tubular member 16. A seal 32 such as an O-ring, is located in annular groove 31 and prevents leakage between inner plug 20' and outer porous tubular member 13.

To prevent leakage, end cap 18 is provided with an annular groove 33 into which is positioned a seal 34, such as an O-ring, which cooperates with the adjacent surface of flange 11 to form a fluid seal therebetween.

Outlet end cap or plate 19 is provided with openings 25, eight in this embodiment, for bolts 23, and with a central threaded opening 35 into which a coupling (not shown) is secured, and is adapted to be connected to a return line (see FIG. 5), to collect the spent culture or reaction medium and cell, catalyst or enzyme products being discharged from the bioreactor, as described hereinafter. Outer end cap 19 also includes an annular groove 36 for retaining a seal 37, such as an O-ring, in a sealing relation with flange 12. Protruding section 21 of end cap 19 is provided with a central countersink 38 in alignment with opening 35 and is adapted to receive an end of porous tubular member 16 and an end 39 of cylindrical core 15 having threads which extend into threaded opening 34.

Cylindrical core 15, in addition to defining the flow channel 17, serves as an exhaust or discharge distributor as the spend medium and cell or enzyme products pass through porous member 16 into the annular channel 17. The core 15, as illustrated in FIG. 3 is of solid construction, but could, if desired, include hollow components. End 39 of core 15 is provided with a plurality (four in this embodiment) of radial, spaced passages or channels 40 and a central opening or passage 41 which provides flow between inner channel 17 and opening 35. The annular channel 17, core 15, radial passages 40, central passage 41 and opening 35 in end cap 19 constitute an outlet collection means.

In the operation of the apparatus of the instant invention as embodied in FIGS. 1-3, the culture or reaction medium is directed through opening 26, grooves 27 and 29, into the annular channel 14 surrounding porous member 13. The medium diffuses through the porous member and flows horizontally in a radial direction through the packing or bed 22 of the support or matrix material with attached, immobilized or adsorbed cells or enzymes. The spent medium and cell or enzyme products (as the case may be) diffuse radially inward through porous member 16 and into the annulus or channel 17, and flow vertically down channel 17 and through the four passages or channels 40 into passage 41 of cylindrical core 15, and emerge from the apparatus via opening 35 whereby the medium and cell or enzyme products are directed as described hereinafter in dealing with FIG. 5.

While the embodiment shown in FIGS. 1-3 illustrate the horizontal flow along a radially inward direction, it should be recognized that the cylindrical arrangement can be modified to direct the horizontal flow along a radially outward direction. Such an arrangement would require modification of the fluid inlet distributor and the fluid component collection assembly. Other fluid distribution inlet means such as those described in copending application Ser. No. 939,557 now abandoned filed Dec. 9, 1986, the specification of which is incorporated herein by reference, may also be used with advantage in the present system. The principle underlying the subject invention is that the flow through the support or matrix bed is in a horizontal direction which overcomes the problems associated with vertical passage of the medium through the bed, as discussed earlier.

For the fluid streamlines through the bed material 22 to be truly horizontal, the axial pressure drops in both annular channels 14 and 17 should be the same. Since the flow rate is the same through porous tubular members 13 and 16, this condition can be achieved by having the same cross-sectional areas in both channels 14 and 17. Thus, if the inner diameter of the cylindrical outer wall 10 is R, and the width of gap or annulus or channel 14 is t, and if the cylindrical core 15 has a diameter r, the width of gap or channel 17, t', may be calculated by equating the two cross-sectional areas such that:

$$t' = \frac{R^2}{2} \frac{(2t-1)}{R}$$

Using this design criterion, a horizontal flow path with minimal short-circuiting of the culture or reaction medium is achieved. While the above formula is a simplified one and works very well for most simple applications, appropriate adjustments may be needed for more complex applications, depending upon the accuracy desired, the contemplated applications and experimental conditions such as temperature, viscosity, density of the solutions etc.

While the components 10, 13, 15 and 16 of the embodiments shown in FIGS. 1-3 have been illustrated and described as being cylindrical, other configurations such as square, hexagonal, octagonal and other shaped configurations may be used. It is understood that the number, shape, size and spacing of the inlet fluid distributor channels or grooves may be changed, eliminated or modified, depending on the configuration of the bioreactor. Furthermore, the embodiment of FIG. 1 can also be modified by replacing the fluid flow distributor arrangement in end cap 18 with an external fluid distributor with one or more lines which are directly connected to the outer annular channels 14 within outer wall 10 (see FIG. 6). In such a case, the openings would extend through the outer wall 10 for attachment to fluid distributor lines, or there may be a single opening in outer wall 10 as in the embodiment of FIG. 6, described herein later. The fluid inlet port may also be located on one side of end cap 18 rather than at the top as illustrated.

In the embodiment illustrated by FIGS. 1-3, by way of example, the porous tubular members 13 and 16 may be constructed of porous polymers such as polyethylene, teflon, polypropylene and the like, or porous sintered metals such as stainless steel, titanium etc., or porous ceramic material or wire or polymer mesh etc., having a porosity of about 5-10 mesh to 0.2 micron, with respective diameters of 0.01 mm and 20 feet, with respective wall thicknesses of 1/64th inch to about 6 inches. The porous member may be replaced with screen or mesh material. The housing or vessel 10 and core member 15 may be constructed of polyethylene or polyacrylic materials, glass, ceramic, stainless steel, aluminum. polycarbonate, polysulfone, polypropylene, titanium and the like, so as to be chemically inert to or compatible with the culture or reaction medium passing therethrough or the cells and enzymes contained therein. The annular channels 14 and 17 may have a radius of 0.01 mm to over 20 feet, depending on the size and dimensions of the bioreactor. The inner plug 20' and protruding section 21 of end cap 19 are constructed of the same material as the housing or may be different so as to be chemically inert to or compatible with the culture or reaction medium passing therethrough or the support or matrix materials, the cells, cell components and enzymes contained therein. The support or matrix materials of bed 22 may consist of beads, mesh or sheets made of inert carrier materials known in the art and include but not limited to silica, alumina, activated charcoal, diatomaceous earth, synthetic resins, zeolites, polyvinylchloride, alginates, carragenans, borosilicate glass, porous ceramic, collagen, gelatin, agarose, polyacrylamide, dextran, agars, and the like, with diameters in the range of 1 micron to about 1 cm. The pressure of the culture or reaction medium is in the range of ambient to about 5,000 psi. The middle channel or chamber in which the support or matrix materials are contained may have a volume of 10 ml to several thousands of liters or gallons, with a height of about ¼ inch to several hundred feet and radius or distance between porous members 13 and 16 of 1/16 inch to about 20 feet or more, depending on the use contemplated.

To fill or pack the middle channel or chamber between the porous or permeable members 13 and 16 with support or matrix material, for example, the inlet cap 18 and inner plug 20' are provided with a pair of aligned openings 42 and 43 having threaded outer end sections for attaching couplings thereto. The support or matrix material is packed or fed into the chamber from a source, not shown, through the openings 42 and 43. The support or matrix material, such as microcarriers, for example, may be inoculated or impregnated with the desired cell culture or the enzyme or enzyme system of choice may be immobilized thereon, prior to packing or such inoculation or immobilization may be carried out after the support or matrix material bed has been packed in the bioreactor.

FIG. 4 illustrates a modification of the arrangement of the porous tubular member 13 and the central core member 15 of FIG. 3, wherein the annular channels 14 and 17 are replaced by a plurality of longitudinally extending grooves spaced around an outer surface of an enlarged outer tubular member 13 and an outer surface of an enlarged core member 15. It is also to be understood that in the construction of large sized columns, the grooves may be replaced by a plurality of hollow members or porous tubes.

For purposes of the illustrated embodiments, similar components will be given corresponding reference numerals. In FIG. 4, an outer porous tubular member 13' has a thickness equal to that of member 13 and annular channel 14 of FIG. 3, and is provided with eight (8) spaced, longitudinally extending grooves 44 (may also be porous tubes) around the outer surface thereof. A central core member 15' is enlarged to a diameter equal to core member 15 and annular channel 17 of FIG. 3, and is provided with four (4) spaced, longitudinally extending grooves 45 around the outer surface thereof, which align with and are in fluid communication with radial passages 40 in the lower threaded end 39 of the core member. Core 15' fits snugly within inner porous member 16'. In this embodiment, the grooves 44 in porous member 13' replace the annular channel 14 of FIG. 3 for directing inlet culture or reaction medium through the member 13 into the bed 22. Similarly, grooves 45 in core member 15' function as and replace outlet annular channel 17 for collecting the spent culture or reaction medium and cell or enzyme products.

With the embodiment of FIG. 4, it is recognized that the reaction or culture medium distribution system illustrated in FIGS. 1 and 2 could be modified to use eight (8) radial grooves or passages 27 and the annular groove or cutaway 29 would be eliminated so that each of the radial passages 27 are aligned with, terminate adjacent to, and are in fluid communication with one of the longitudinal groove 44 of porous tubular member 13,.

The inlet distribution means in FIG. 4 is comprised of the central opening and radial grooves, as in FIG. 3, in combination with the vertical grooves 44 in porous member 13', while the outlet collection means consists of the vertical grooves 45 in core member 15', and radial passages 40, central passage 41 and threaded opening 35 as in FIG. 3. The size and diameter of these grooves or openings, as the case may be, are determined by the particle size of the matrix material used and the contemplated application, such that the matrix particles would not pass through the grooves or openings, along with the culture or reaction medium, into the outlet channel.

The internal and external dimensions of the bioreactor may be varied over a wide range depending upon the size of the bioreactor desired and the particular application desired or contemplated, as illustrated earlier.

FIG. 5 illustrates an embodiment of a continuous cell-culture or enzyme reaction scheme using a radial flow, microcarrier based bioreactor of this invention. A bioreactor (or cell culture growth or enzyme reaction chamber) 50, constructed as described earlier is provided with a medium input line 51 and an output line 52 for spent cultures or reaction medium and/or cell or enzyme products. Input line 51 is connected by a line 53 to a pump 54 via a valve 55 of an on-line sampling mechanism 56, with pump 54 being connected via a line 57 to a stirred vessel 58. Output line 52 is connected via a valve 59 to an on-line sampling mechanism 60, and is connected to a line 61 which splits into lines 52 and 63, with line 62 being connected to stirred vessel 58 and line 63 being connected to form a product stream, as indicated by legend. Stirred vessel 58 is provided with a stirring mechanism 64 therein driven by means, not shown, such as an electric motor, and is connected by line 65 and 66 to a fresh culture or reaction medium supply and to an air/$CO_2$ supply, indicated by legend. In addition, a pH detector or monitor 67 and a dissolved $O_2$ detector or monitor 68 are connected to stirred vessel 58.

Figure 6:
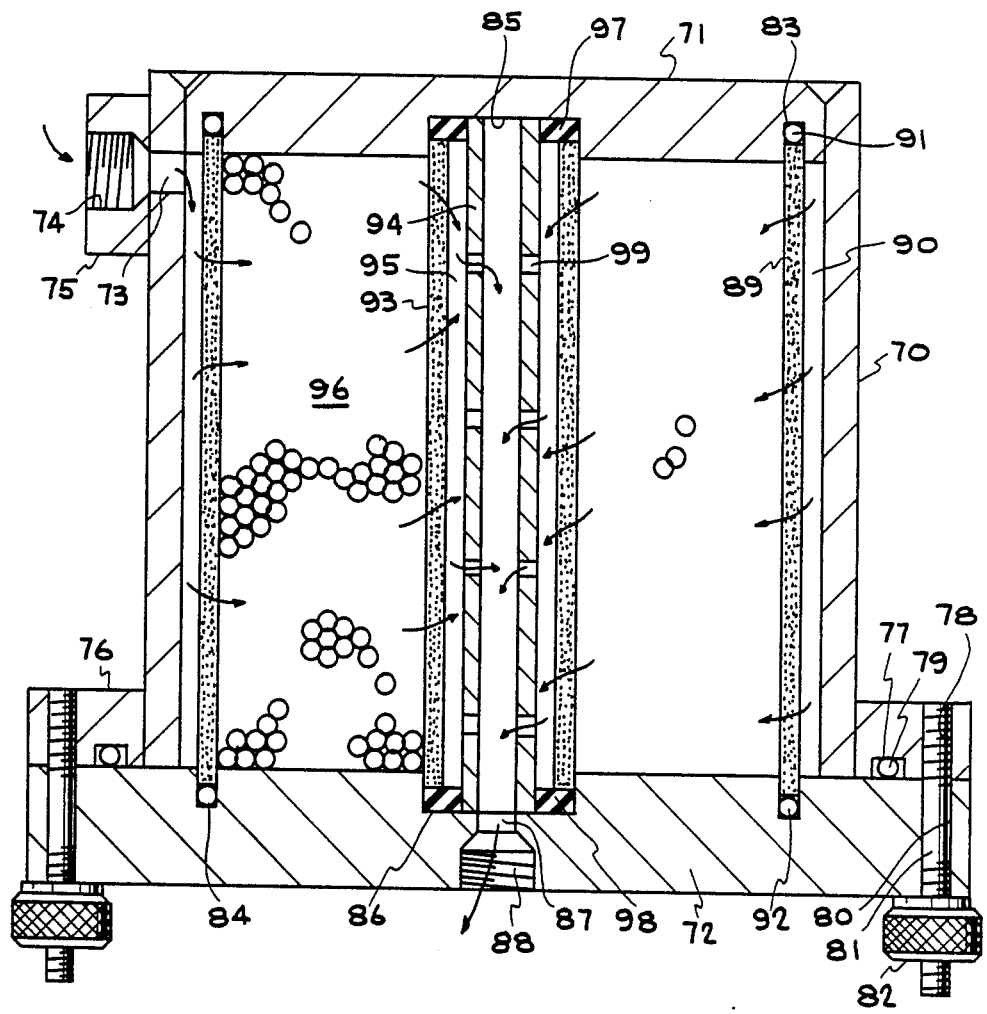
FIG. 6 illustrates another embodiment of a radial flow bioreactor of the present invention wherein the reaction or culture medium enters through a port provided in the side of the bioreactor and uniformly flows in a horizontal (radial) direction across the matrix bed.

Referring now to FIG. 6, which illustrates an embodiment wherein the culture or reaction medium is directed through a side opening rather than an opening at the top as in FIG. 1, and wherein only one removable end plate, cap or member is provided, the bioreactor basically comprises a housing or vessel formed by an outer cylindrical wall 70, an end plate or member 71 secured to wall 70 as by welding or other securing means, with outer wall 70, end 71 and end cap 72 forming a chamber within which are contained various components similar to those of the embodiment of FIG. 1, and described in detail hereinafter.

Outer wall 70 is provided with an inlet port or opening 73 which is aligned with a threaded opening 74 of collar or member 75 secured to wall 70. An outwardly extending flange 76 is secured (such as by welding, or other securing means or methods) to or integrated with an end of outer wall 70 opposite end plate 71 and is provided with an annular groove 77 and a plurality of threaded apertures 78 (eight in this embodiment). A seal 79, such as an O-ring, is located in groove 77 to prevent leakage between wall 70 and end cap 72.

End cap 72 is provided with a plurality of apertures 80 (eight in this embodiment) through which threaded bolts 81 extend and are secured at one end thereof in threaded apertures 78. Thumb screws or nuts 82 are threaded onto bolts 81 and secure end plate 72 tightly against outer wall 70 and flange 76.

End plate 71 and end cap 72 are provided on the inner surfaces thereof with annular grooves 83 and 84 and with centrally located countersink portions 85 and 86, with end cap also being provided with an opening 87 in alignment with countersink 86 having an enlarged threaded outer section 88. An outer tubular porous member or filter screen 89 is retained in grooves 83 and 84, so as to define an outer annular channel or passage 90 between tubular member 89 and outer wall 70. Seals 92 and 92, such as O-rings, are located in grooves 83 and 84 at opposite ends of tubular member 89 to prevent leakage around the ends thereof. An inner porous tubular member 93 and a hollow core member 94 are retained in countersinks 85 and 86 in a spaced relation so as to define an inner annular channel or passage 95 therebetween. A bed or matrix of packing or support material 96 of selected materials, as described herein earlier, is located between porous tubular members 89 and 93. To retain core member 94 in alignment with opening 87 of end cap 72 and to prevent leakage around the ends of tubular member 93, a pair of hollow spacer seals 97 and 98 are located in countersinks 85 and 86, and extend around ends of core member 94. Hollow core member 94 is provided with a plurality of openings 99 spaced along the length thereof. The size, width, diameter or dimensions of the openings 99 or grooves 83 and 84 are determined by the particle size of the matrix material used, the size of the bioreactor and the particular application. The size of these openings or the width of the grooves should be so adjusted or chosen that the particles of the matrix material do not pass through the openings or grooves along with the culture or reaction medium into the collection port or outlet.

In operation of the embodiment of FIG. 6, reaction or culture medium from an external supply source is directed, as shown by flow arrows, through 73 into annular channel 90 which then diffuses through porous tubular member 89 and flows radially through bed 96. The spent medium, reaction products or other materials then diffuse through inner porous tubular member 93 and into inner channel 95 and pass through passages 99 and the hollow portion of core member 94 into opening 87 where it is directed to a point of use or collection as described previously.

While only one inlet port or opening 73 and collar 75 are shown, the apparatus may be provided with a plurality of such openings or collars in spaced relation around wall 70. Although the inlet port or opening 73 is shown in FIG. 6 as being located at or near the top end and outlet port or opening 87 at or near the bottom or lower end this arrangement or the relative positions of the inlet and outlet openings may be reversed, depending on the particular use, the operating pressure of the system and other parameters determined on a case by case basis. Furthermore, the embodiment of FIG. 6 may be of a square configuration with the outer and inner tubular members 89 and 93 being each replaced with four sheets of the same material with adjacent ends or sides sealed to prevent leakage at the corners, and with core member 94 being formed in a square cross-sectional configuration. Grooves 83 and 84 and countersinks 85 and 86 would be accordingly modified to support the square configuration.

Figure 7:
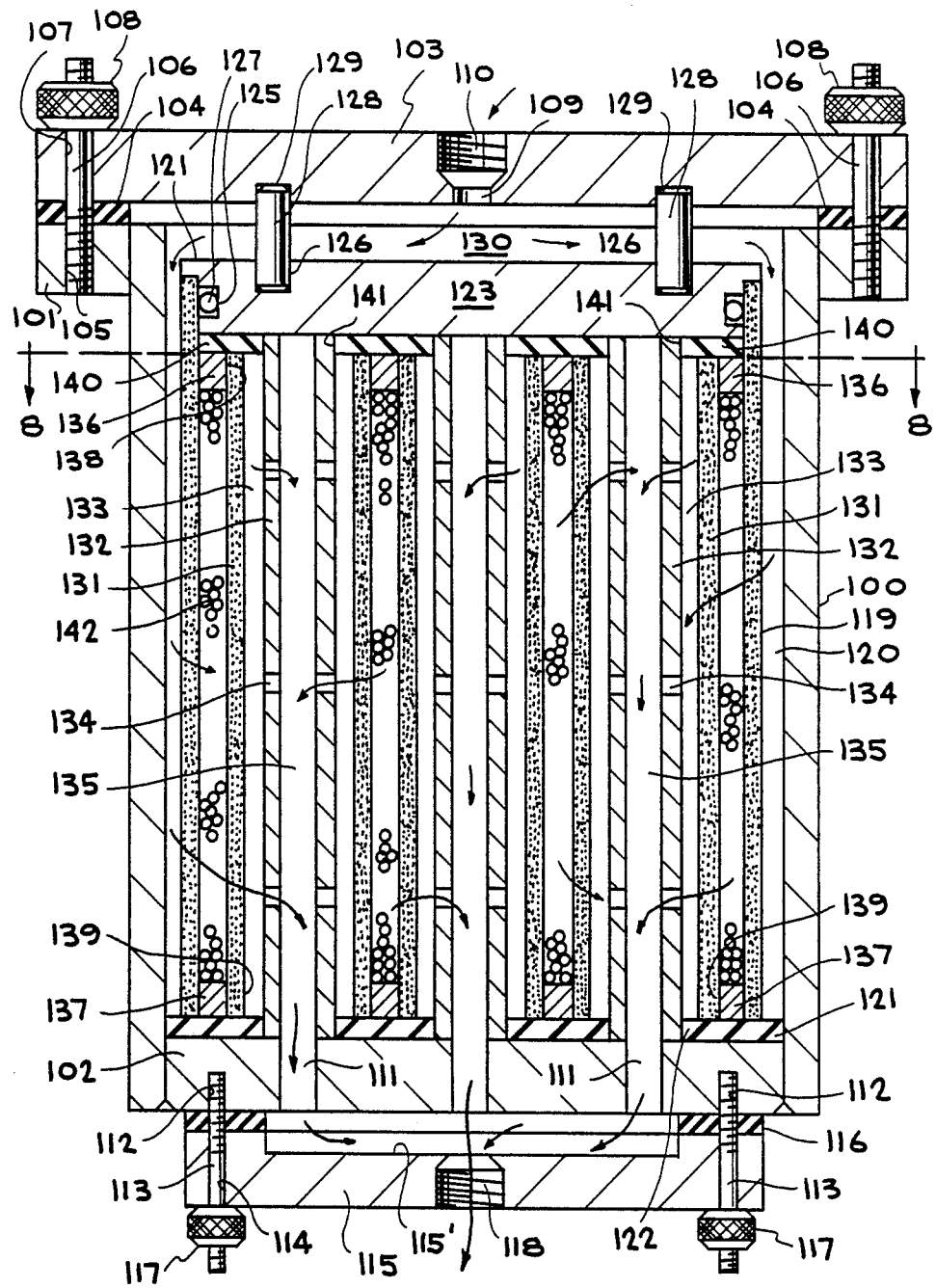
FIG. 7 illustrates in cross-section another embodiment of the invention, similar to that of FIG. 1 but which utilizes a plurality of spaced inner porous tubes and inner channels, taken along line 7—7 of FIG. 8.
Figure 8:
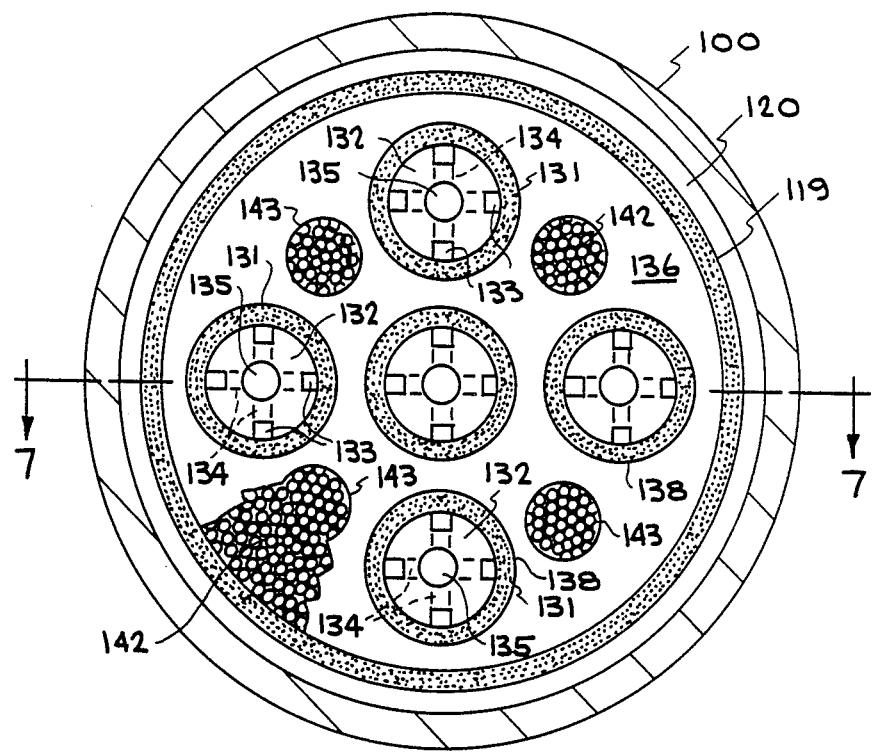
FIG. 8 is a view of the apparatus of FIG. 7 taken along line 8—8 of FIG. 7.

The embodiment illustrated in FIGS. 7 and 8 is for large capacity applications and in circumstances where larger particle size of the matrix material is desired (such as, for example, glass, ceramic or polymer beads of the size in excess of a few tenths of a millimeter or larger). It is generally similar in operation to the FIG. 1 embodiment except that it is provided with a plurality of optional, spaced inner porous tubular members and cooperating core members so as to provide a plurality of outlet flow rather than a single central outlet flow as in the embodiment of FIG. 1. Although the illustration of this embodiment, as shown in FIG. 7, is provided with a plurality of inner porous tubular members and cooperating core members, with the use of the inner porous tubular members, the core members may be superfluous and may be eliminated. Alternatively, the use of the solid core members provided with a plurality of holes or grooves, may render the additional inclusion of the inner porous tubular members superfulous and thus dispensable. That is, in this embodiment, either the inner porous tubular members and the core members may be eliminated without affecting in any manner the mode of operation of the bioreactor. Furthermore, if for any reason, a two stage filtration step is desired to contain the separation material between the outer and inner porous tubular members, depending on the use contemplated and the separation media employed, the inner porous tubular members may be positioned or located inside or within the central core members, if these core members are hollow and provided with a plurality of holes or grooves. As shown in FIGS. 7 and 8, the bioreactor housing or vessel is basically composed of an outer cylindrical wall 100 having an outwardly protruding flange 101 secured, as by welding, or other securing means or methods, at one end or made integral with the wall, an end plate or plug member 102 secured, as by welding or other securing means or methods, in the opposite end of outer wall 100, and an end cap or plate 103 removably attached to flange 101 via a gasket or seal 104. Flange 101 is provided with a plurality of threaded openings 105 (twelve to sixteen in this embodiment) into which are inserted threaded bolts or studs 106 which extend through openings 107 in end cap 103 and aligned openings in gasket 104. Thumb screws, nuts, bolts or other means 108 are threaded onto studs 106 for removably securing end cap 103 to flange 101. End cap 103 is provided with a centrally located opening or passage 1109 having a threaded section 110 for attachment to a source of material, as in FIG. 5.

End plate or plug member 102 is provided with a plurality of openings or passages 111, five in this embodiment, and a plurality of threaded holes 112 (twelve in this embodiment) into which are inserted threaded studs or bolts 113. Studs 113 extend through openings 114 in a fluid collector cap 115 via openings in a gasket or seal 116, and thumb screws, nuts or bolts 117 secure the collector cap 115 to plug member 102. Collector cap 115 is also provided with a countersink section 115' on the inner surface thereof and with a threaded opening 118, which is adapted for attachment to a stream of reactant, product or other material.

A porous tubular member 119, such as that described in the embodiments of FIGS. 1 and 6, for example, is positioned within outer wall 100 so as to define a space therebetween forming an annular inlet channel 120. A gasket or seal 121 having apertures 122, which align with openings or passages 111 of plug member 102 is located intermediate a lower end of tubular member 119 and plug member 102. A support plate or plug 123 having an outer flange section 124, annular groove 125 and a plurality of holes or countersinks 126 is positioned in and over an upper end of tubular member 119, with a seal 127, such as an O-ring, located in groove 125, preventing leakage therebetween. A plurality of dowels or members 128 are mounted in holes 126 and extend into holes 129 in end cap 103 to prevent movement of porous tubular member 119 and to maintain a gap 130 between end cap 103 and support plug 123, which functions as the inlet fluid fluid medium distributor from passage 109 to annular channel 120, as shown by flow arrows. If desired, the holes 129 in end cap 103 may be replaced with a groove into which one end of dowels 128 extend.

Within outer porous tubular member 119, a plurality of smaller diameter porous tubular members 131 are positioned in spaced relation (see FIG. 8 where five are shown). Within each tubular member 131 is a hollow core member 132 having a plurality of spaced grooves 133 around the outer surface and a plurality of spaced radial openings or passages 134 along the length thereof which interconnect grooves 133 with a hollow passageway 135. Each of core members 132 is mounted in a tubular member 131 so as to abut thereagainst to provide support for the tubular members, as in the embodiment of FIG. 4, with the grooves 133 forming collection flow channels. A pair of retainer plates 136 and 137 are positioned within outer tubular member 119 and at each end of inner tubular members 131 to retain tubular members in spaced relation, retaining plates 136 and 137 being provided with a plurality of openings 138 and 139 into which the end of tubular members 131 extend. Tubular members 131 abuts at the lower ends thereof against the gasket or seal 121, having apertures 122 therein, and at the upper ends thereof against a gasket or seal 140 having apertures 141 therein, whereby leakage around the ends of the tubular members is prevented. Core members 132 extend at each end into apertures 122 and 141 of gaskets 121 and 140, and are retained such that hollow passageways 135 thereof are aligned with openings or passages 111 in plug member 102.

A reactor bed, packing or matrix 142 of selected support material, as in the embodiments of FIGS. 1 and 6, is located intermediate retainer plates 136 and 137 and between outer tubular member 119 and each of tubular members 131, retaining plate 136 being partially cut away in FIG. 8 to show the material of bed 142. Retainer plate 136 is also provided with a plurality of apertures 143 (see FIG. 8) through which the medium 142 can be inserted or introduced, if desired, by providing end cap 102, support plug 123 and gasket 140 with corresponding apertures as in the embodiment of FIG. 1.

In the embodiment of FIGS. 7 and 8, the fluid or medium inlet distribution system comprises inlet passage 109, gap 130, and annular channel 120, while the medium collection system comprises grooves 133, radial openings 134, and hollow passageways 135 each of core member 132, openings 111 in end plug 102, countersink 115' and opening 118 in collector cap 115. Passage of the medium through the bioreactor of FIG. 7 is illustrated by flow arrows, with the medium flowing in a radial or horizontal direction through the bed 142, as in the embodiment previously described.

While the embodiment of FIGS. 7 and 8 utilizes five (5) inner porous tubular/core members, such a number is for purposes of illustration only and any number of such components may be used depending on the size or dimensions of the overall bioreactor.

The porous tubular members of the embodiment of FIGS. 7 and 8 have been illustrated and described as being cylindrical in configuration but such a description is not intended to limit the invention to that configuration as both or either of the outer or inner tubular members may of another or different configuration such as triangular, octagonal, hexagonal, square configurations, for example. Furthermore, it is within the scope of this embodiment to introduce the fluid medium into a centrally located tubular member of the apparatus and have it flow horizontally or radially outward to and a plurality of spaced tubular members and core members for treatment or reaction and collection and products as the case may be and functions in the same manner as described herein previously.

Figure 9A:
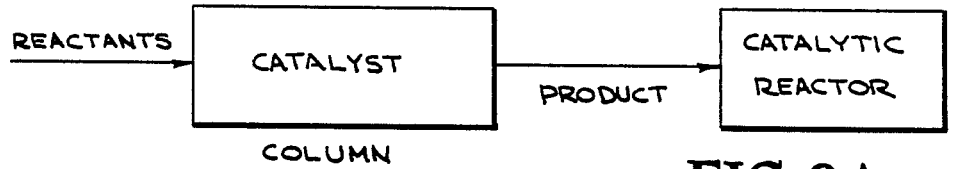
FIG. 9A through 9F illustrate the various applications or uses of the apparatus of the invention.
Figure 9B:
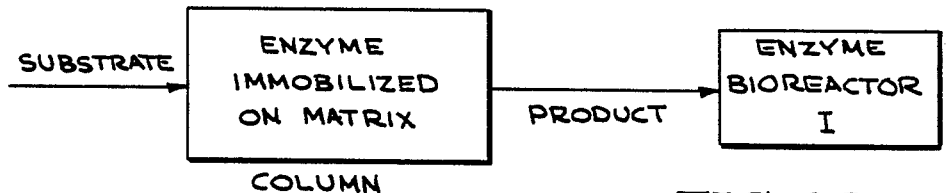
Figure 9C:
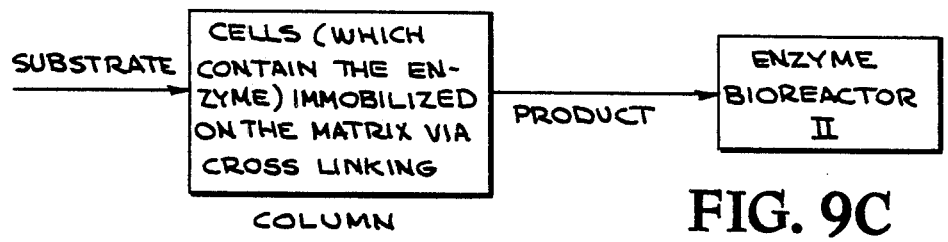
Figure 9D:
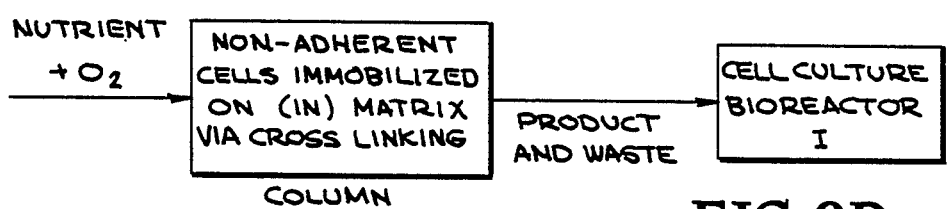
Figure 9E:
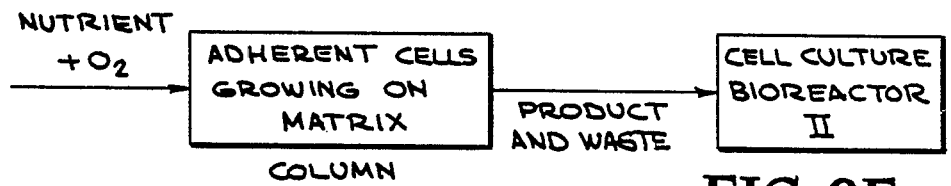
Figure 9F:
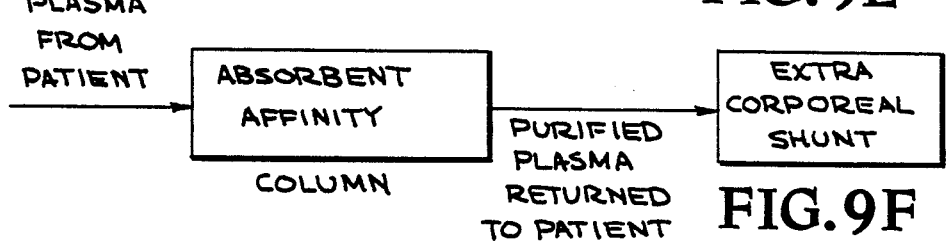

FIGS. 9A through 9F illustrate in block diagrams various applications for the embodiments of the bioreactor of the present invention. FIG. 9A illustrates the use of the bioreactor as a catalytic reactor where the packed bed is impregnated with a catalyst of choice, such as platinum palladium, nickel etc., and the reactants are directed across the packed bed where they are converted to products. The products are then collected as needed. FIG. 9B illustrates the use of the bioreactor as an enzyme bioreactor of Type I, where an isolated enzyme, with or without cofactors, is immobilized on the support material and a substrate stream is directed across the bed where they are converted by the enzyme into the desired products, which are then removed. In FIG. 9C is depicted the bioreactor as an enzyme reactor of Type II, with whole cells (containing the enzyme of choice) are immobilized on the support material. A flow of the substrate is then directed across the bed of cells where the substrate is converted into the desired products. In FIG. 9D is illustrated, the bioreactor functioning as a cell culture chamber for non-adherent cells immobilized on the support material contained in the chamber, by methods such as cross-linking or covalent bonding. Appropriate reactants, nutrients for the cells and oxygen, if necessary for growth, are supplied to the chamber. The reaction products and cell waste materials are then removed from the chamber by methods described herein earlier. In FIG. 9E, the bioreactor functions as a cell culture chamber for adherent cells which adhere to and grow on the support or matrix material. As in FIG. 9D, reactants, nutrients, oxygen, if necessary, are supplied to the cells in the chamber. The products and waste materials are removed as before, In FIG. 9F, the bioreactor is used as an extracorporeal shunt for use in hospitals and for clinical care. Body fluids, such as plasma, from a patient is directed across the bed of support materials which are used in adsorbent or affinity chromatography. The undesirable materials or toxic wastes in the body fluid is adsorbed on to the packing material in the column and are thus removed from the body fluid, which is then returned to the patient.

While the foregoing description of the drawings illustrate various embodiments and applications of the bioreactor of the present invention, the following examples are presented by way of illustration only to demonstrate the operation and effectiveness of the subject bioreactor and are not to be construed as limiting the invention to the specific examples described or to the precise mode of operation.

EXAMPLE 1

To illustrate the use of the bioreactor of the instant invention for the growth of cells or cell cultures, the bioreactor is packed with swollen cytodex microcarriers at a density of about 55 g/l. Suspended cells are inoculated through the medium inlet port and allowed to attach to the microcarriers. Seeded culture chambers are then placed in the bioreactor loop and monitored daily.

The properties of the culture chamber are investigated by experiments with two different cell types, diploid human fibroblasts and MDCK cells, and two different culture media, Dulbecco's Modified Eagle's Medium (DMEM) with 10% fetal bovine serum and serum-free Ventrex medium.

EXAMPLE 2

Cell Yield Experiments

Duplicate bioreactors are seeded and carried for seven days. Lactate production and glucose consumption are monitored daily. At the end of the culture period, the cell number achieved by each culture is determined by trypsinization of the entire contents of the reactor and enumeration with a hemacytometer. The viability of the cells is determined by the trypan blue dye exclusion method.

Lactate production and glucose utilization are charted as evidence of increased cell metabolism and as an indirect means of estimating cell mass. The cell count and viability data are used to calculate cell densities for the different cell types and media used. These data are compared with reports in the literature for other culture chambers in order to evaluate the efficacy of the radial flow unit.

The trypsinization procedure needed for the cell counts is a tedious one and requires repeated washings and additional enzyme treatments before acceptable cell removal is achieved. However, it is believed that direct determination of cell yields provides the greatest credibility for evaluation of the culture chamber.

EXAMPLE 3

Culture saturation Experiments

In order to determine maximum cell densities obtainable, four replicate culture chambers are seeded and maintained under the standard conditions established during the preceding experiments. Lactate and glucose utilization data are collected daily. Individual reactors are terminated after 3, 7, 10 and 14 days of culture, and cell counts are made using the trypsinization procedure. Where necessary, the experiment is repeated using different time intervals for culture counting until a plateau in cell production was achieved. Cell yield and cell viability data are correlated to lactate and glucose determinations. The maximum cell number achievable is taken to be that observed within the stable plateau phase. Although the small number of replicate cultures used is not sufficient to provide the statistical accuracy obtainable in cell saturation studies with smaller culture systems or suspension cultures, the logistics of handling large-scale bioreactors make this compromise necessary. Maximum cell densities observed are compared with reports in the literature for other mass culture systems.

The following tabulation provides a comparison chart of culture methods for anchorage-dependent cell culture. In the table, the surface area and cell density calculations are based on reports in the literature. The figures given for the radial-flow bioreactor are based on a surface area cell coverage factor equal to that used in the methods described above.

TABLE

Comparison Chart Of Culture Methods For Anchorage-Dependent Cell Cultures

| Method | Surface Area $(cm^2)$/ Liter of Bioreactor | Cell Density Cells/l of Bioreactor |
| --- | --- | --- |
| Roller Bottles | $3.6 \times 10^2$ | $7.3 \times 10^7$ |
| Glass Beads | $2.5 \times 10^4$ | $5.0 \times 10^9$ |
| Microcarriers in Suspension | $6.0 \times 10^3$ | $1.2 \times 10^9$ |
| Hollow Fibers | $1.6 \times 10^4$ | $1.0 \times 10^{10}$ |
| Ceramic matrix | $3.2 \times 10^4$ | $2.2 \times 10^{10}$ |
| Radial Flow Bioreactor | $3.3 \times 10^5$ | $6.6 \times 10^{10}$ |

With the radial flow bioreactor of this invention, scale-up can be easily carried out and will provide superior performance compared to exiting technology, in order to increase the production of cultured cells, all that is necessary is to increase the height of the cell column. Since the cell bed height would not be changed by this modification, the path-length of the medium through the cells should also not change. There should, therefore, be minimal problems with the pressure drops, anoxia and media gradients characteristic of other scaled-up systems.

EXAMPLE 4

Scale-Up Experiments

To test the ease with which radial flow chambers can be scaled up, a column with a 5 liter volume is placed in the bioreactor loop and maintained as described earlier. The unit is trypsinized on the day the cells reach saturation in the earlier experiments, which are conducted with half liter units. Cell count data are correlated with metabolic indicators, and cell densities achieved by the scaled-up units are compared with data from the half-liter chamber experiments to gauge the efficiency of the scale-up process.

It has thus been shown that the present invention provides a bioreactor which has substantially advanced the state of the art. This is due in large measure to the horizontal or radial flow and distribution of the culture medium through the bed of microcarriers with cells attached thereto or with enzymes immobilized thereon. The radial-flow bioreactor of this invention overcomes the problems of the prior known methods and devices discussed earlier, especially when scale-up is undertaken for the large-scale production and maintenance of attachment or anchorage-dependent cells.

The foregoing description of the preferred embodiments of the present invention have been presented for purposes of illustration and description and for a better understanding of the invention. It is not intended to be exhaustive or to limit the invention to the precise form disclosed; and obviously many modifications and variations are possible in light of the above teaching. The particular embodiments were chosen and described in some detail to best explain the principles of the invention and its practical application to thereby enable others skilled in the relevant art to best utilize the invention in various embodiments and with various modifications as are suited to the particular use contemplated. It is intended to cover in the appended claims all such modifications, variations and changes as fall within the scope of the invention.

What is claimed is:

1. A radial-flow bioreactor comprising:
   a vessel having at least one removable end section having a reaction medium inlet therein, said removable end section including a protruding section provided with a cut-away section extending around a periphery thereof,
   a plurality of spaced porous members located within said vessel,
   a bed of support material located within said vessel and intermediate said spaced porous members,
   a distribution means located in said removable end section and having a centrally located opening in fluid communication with said inlet and said cut-away section of said removable end section for directing reaction medium substantially uniformly radially outwardly and about an outer surface of a first of said plurality of porous members on a side opposite said bed of support material, and
   an outlet collection means for collecting at least spent reaction medium and discharging such from said vessel being partially located on a side of a second of said plurality of porous members opposite said bed of support material,
   whereby reaction medium passing through said inlet and said distribution means passes uniformly in a substantially radial inward direction through said first of said porous members, substantially radially inward through said bed of support material, and substantially inward through said second of said porous members into said inlet collection means.

2. The bioreactor of claim 1, wherein said vessel comprises a housing having a wall section defining a chamber and having an outwardly extending flange section on at least one end of said wall section, wherein said removable end section includes a protruding section constructed to at least partially extend into one end of said wall section, and additionally including sealing means located between said removable end section and said flange section of said housing, and means for removably securing said removable end section to said outwardly extending flange section of said housing.

3. The bioreactor of claim 2, wherein said reaction medium inlet in said removable end section is a substantially centrally located opening, and said removable end section having a plurality of spaced radially extending grooves located on a surface of said protruding section of said removable end section, said grooves extending outwardly from said opening.

4. The bioreactor of claim 3, wherein said plurality of spaced radially extending grooves terminate at said cut-away section.

5. The bioreactor of claim 4, wherein said spaced porous members are annular and are coaxially positioned with respect to one another, an outer one of said coaxial porous members being positioned in said chamber of said housing and spaced from said wall section of said housing so as to define an outer annular channel therebetween, whereby said central opening, said radially extending grooves, said cut-away section and said outer annular channel constitute said inlet distribution means.

6. The bioreactor of claim 5, wherein an inner one of said coaxial porous member is positioned around and in spaced relation with a core member positioned substantially centrally within said chamber to define an inner annular channel therebetween, said core member being provided with a central passageway in at least one end thereof and a plurality of passageways extending from an outer surface of said core member and in fluid communication with said central passageway of said core member, said central passageway being in fluid communication with an outlet opening in said housing, whereby said inner annular channel, said plurality of passageways in said core member, said central passageway of said core member, and said central outlet opening in said vessel constitute said outlet collection means.

7. The bioreactor of claim 6, additionally including an annular plug member positioned in said chamber of said housing and adjacent said protruding section of said removable end section, said plug member being provided with a centrally located countersink section on one side thereof and constructed to at least partially fit within said outer porous member, one end of said inner porous member and an opposite end of said core member extend into said countersink section of said plug member, and seal means located intermediate said plug member and said outer porous member.

8. The bioreactor of claim 7, wherein said removable end section and said plug member are provided with at least one aligning opening extending therethrough.

9. The bioreactor of claim 7, wherein said housing includes a second outwardly extending flange section secured to an opposite end of said wall section, and additionally including a second removable end section having an annular protruding section and removably secured to said second flange section, said protruding section being constructed to at least partially extend into said wall section of said housing, and seal means located intermediate said second end section and said second flange section, said second flange section, said outlet opening in said housing extending through and substantially centrally located in said second removable end section.

10. The bioreactor of claim 9, wherein said protruding section of said second removable end section is provided with a centrally located countersink section, and wherein said one end of said core member and an opposite end of said inner porous member extend into said countersink section of said protruding section.

11. The bioreactor of claim 10, wherein said one end of said core member is removably secured in said outlet opening in said second removable end section.

12. The bioreactor of claim 10, wherein said outer porous member is retained within said chamber of said housing between said protruding sections of said removable end sections of said housing.

13. The bioreactor of claim 3, wherein said spaced porous members are annular and are coaxially positioned with respect to one another, an outer one of said coaxial porous members being positioned in said chamber and snugly adjacent said wall section of said housing, said outer porous member being provided with a plurality of spaced longitudinally extending grooves on an outer surface thereof, said longitudinally extending grooves being constructed and positioned to align with said radially extending grooves of said protruding section of said removable end section of said housing, whereby said central opening, said radially extending grooves, and said longitudinally extending grooves constitute said inlet distribution means.

14. The bioreactor of claim 13, wherein said inner porous member is positioned snugly adjacent an outer surface of said core member positioned centrally within said chamber, and wherein said core member is provided with a plurality of spaced, longitudinally extending grooves in an outer surface thereof, said core member being provided with a central opening in at least one end thereof and a plurality of passageways extending from said grooves into said central opening, whereby said longitudinally extending grooves, said plurality of passageways, said central opening and said outlet opening in said vessel, constitute said outlet collection means.

15. The bioreactor of claim 14, wherein said bed includes microcarriers which are impregnated with cells or cell cultures.

16. The bioreactor of claim 14, wherein said bed includes microcarriers which have an enzyme or enzyme system immobilized thereon.

17. The radial-flow bioreactor of claim 1 in combination with a continuous cell-culture system, said system including:
   a stirred vessel containing culture-medium,
   a pump operatively connected to said stirred vessel and to said inlet distribution means of said bioreactor for directing fresh culture medium into said bioreactor,
   an on-line sampling means operatively connected between said pump and said bioreactor,
   said stirred vessel being operatively connected to said outlet collection means of said bioreactor for receiving spent culture medium from said bioreactor,
   an on-line sampling means operatively connected between said stirred vessel and said bioreactor,
   means for producing a product stream operatively connected to said outlet collection means of said bioreactor, and
   means for supplying fresh culture medium and air or $CO_2$ to said stirred vessel.

18. The combination of claim 17, additionally including means connected to said stirred vessel for monitoring pH and dissolved $O_2$ of the culture medium therein.

19. The bioreactor of claim 1, wherein said vessel includes a wall section removably secured at one end to said removable end section and a plug section fixedly secured to an opposite end of said wall section.

20. The bioreactor of claim 19, wherein said outlet collection means is operatively connected to said plug section of said vessel.

21. The bioreactor of claim 1, wherein said vessel comprises a housing having a wall section defining a chamber, a removable end section, and a plug section; said removable end section constituting said removable end section of said vessel and being removably connected to one end of said housing; said plug section being fixedly secured to an opposite end of said housing; sealing means positioned intermediate said wall section and said removable end section of said housing to prevent leakage therebetween; and means for removably securing said removable end section to said one end of said housing.

22. The bioreactor of claim 31, wherein said spaced porous members are located in said chamber and have ends thereof extending into openings in each of said removable end sections and said plug section of said housing for retaining said porous members in spaced relationship, an outer porous member of said spaced members being located in a spaced relation to said wall section, said bed being contained in a space intermediate said porous member and intermediate said removable end section and said plug section of said housing.

23. The bioreactor of claim 24, wherein said inlet distribution means is operatively connected to at least one opening in said wall section of said housing.

24. The bioreactor of claim 22, wherein and inner porous member of said spaced porous members being positioned around a core member retained between said removable end section and said plug section of said housing, said core member having at least a passage therein in communication with an opening in said removable end section, said outlet collection means being operatively connected to said removable end section.

25. The bioreactor of claim 24, wherein said core member is hollow forming a passageway, has a plurality of spaced longitudinally extending grooves around an outer surface thereof, and has a plurality of radially extending openings interconnecting said grooves with said passageway, said passageway being in alignment with said opening in said removable end section of said housing, said grooves, openings and passageways of said core member and said opening in said removable end section constituting said outlet collection means.

26. The bioreactor of claim 1, wherein said spaced porous members comprise an outer porous member and a plurality of inner porous members positioned in spaced relation to each other and in spaced relation to said outer porous member, said outer porous member having said distribution means in fluid communication with one side thereof, each of said plurality of inner porous members having said outlet collection means in fluid communication with one side thereof, said bed of support material being located intermediate opposite sides of said outer and inner porous members.

27. The bioreactor of claim 26, wherein said outer porous member and each of said plurality of inner porous members are of an annular configuration.

28. The bioreactor of claim 26, additionally including means for retaining said plurality of inner porous members in spaced relation with each other and with said outer porous member.

29. The bioreactor of claim 26, additionally including a core member positioned within each of said inner porous members, each of said core members being with fluid passage means operatively connected to at least one fluid outlet of said vessel and constituting said outlet collection means.

30. The bioreactor of claim 29, wherein each of said core members include a longitudinally extending passageway and a plurality of longitudinally extending slots around an outer surface thereof, and a plurality of openings interconnecting said slots with said passageways.

31. The bioreactor of claim 26, wherein said vessel comprises a housing defining a chamber and having a wall section closed at one end by a plug member having a plurality of openings therein, and closed at an opposite end by a removable cap member having at least one opening therein, said plurality of porous members being retained in spaced relation with said chamber between said plug member and a retainer member mounted in spaced relation to said cap member to define a gap therebetween, and seal means provided between said plug member and one end of said porous members and between said retainer member and opposite ends of said porous members.

32. The bioreactor of claim 31, wherein one of said plurality of porous members is positioned in spaced relation with said wall section of said housing so as to define a channel therebetween; said opening in said cap member, said gap between said cap member and retainer member, and said channel constituting said inlet distribution means.

33. The bioreactor of claim 22, wherein other of said plurality of porous members are positioned within said one of said porous members in spaced relation therewith and in spaced relation with each other, and additionally including a core member within each of said other of said plurality of porous members, said core member having a plurality of fluid passages therein and located such that said passages are in fluid communication with said plurality of openings in said plug member.

34. The bioreactor of claim 33, wherein each of said core members includes at least one passageway therein in open communication with said plurality of fluid passages, said passageway of each core member being in alignment with an opening in said plug member, said outlet collection means including said fluid passages, said passageway and said openings.

35. The bioreactor of claim 34, additionally including a collector cap secured to said plug member and including an opening therein, said collector cap being constructed so as to provide open communication between said opening thereon and said plurality of openings in said plug member.

36. A method for developing anchorage-dependent cells comprising the steps of:

forming a vessel having a chamber therein and an inlet and an outlet for allowing culture medium to pass through said chamber,
providing said vessel with a removable end section, the removable end section including a protruding section provided with a cut-away section extending around a periphery thereof,
providing said chamber with spaced porous members to define a middle chamber therebetween,
providing the middle chamber with a bed of support material with cells attached thereto,
providing means in flow communication with the inlet and located in said removable end section and said cut-away section of said removable end section for distributing culture medium uniformly on an outer surface of one of the spaced porous members opposite the support material,
providing means for collecting at least spent culture medium on an inner surface of another of the spaced porous members opposite the spent material,
directing culture medium inwardly through the bed of support material in a substantially radial direction for growth or development of the cells attached to the support material, and
collecting at least spent culture medium after such has passed substantially radially through the spaced porous members and the bed of support material therebetween.

37. The method of claim 36, wherein the step of directing the culture medium is carried out by positioning the porous members in spaced coaxial relation, uniformly distributing the culture medium about an outer surface of the spaced coaxial porous members, and directing the culture medium substantially radially inward through the outer porous member, the bed of support material, and the inner porous member, whereafter at least the spent culture medium is collected by the collecting means.

* * * * *

UNITED STATES PATENT AND TRADEMARK OFFICE
CERTIFICATE OF CORRECTION

PATENT NO. : 4,833,083
DATED : May 23, 1989
INVENTOR(S) : VINIT SAXENA

It is certified that error appears in the above—identified patent and that said Letters Patent is hereby corrected as shown below:

Title Page, Column 1, Lines 5, 6 and 7 should read:

-- Notice: The portion of the term of this patent subsequent to December 9, 2003 has been disclaimed. --

Signed and Sealed this

Fifteenth Day of October, 1991

Attest:

HARRY F. MANBECK, JR.

*Attesting Officer*         Commissioner of Patents and Trademarks